US009485918B2

(12) United States Patent
Versteylen et al.

(10) Patent No.: US 9,485,918 B2
(45) Date of Patent: *Nov. 8, 2016

(54) TREATMENT SYSTEM TO PROLONG LIFE OF CUT FLOWERS

(75) Inventors: Sayandro Versteylen, Fontana, CA (US); Ronald Jensen, Chicago, IL (US); Lindsay A. Riehle, Beaumont, CA (US)

(73) Assignee: PAPER-PAK INDUSTRIES, Laverne, CA (US)

( * ) Notice: Subject to any disclaimer, the term of this patent is extended or adjusted under 35 U.S.C. 154(b) by 247 days.

This patent is subject to a terminal disclaimer.

(21) Appl. No.: 13/696,659

(22) PCT Filed: May 13, 2011

(86) PCT No.: PCT/US2011/036446
§ 371 (c)(1),
(2), (4) Date: Nov. 7, 2012

(87) PCT Pub. No.: WO2011/143564
PCT Pub. Date: Nov. 17, 2011

(65) Prior Publication Data
US 2013/0074402 A1 Mar. 28, 2013

Related U.S. Application Data

(60) Provisional application No. 61/334,488, filed on May 13, 2010.

(51) Int. Cl.
A01G 5/06 (2006.01)
B65D 85/50 (2006.01)
A01N 3/02 (2006.01)

(52) U.S. Cl.
CPC . *A01G 5/06* (2013.01); *A01N 3/02* (2013.01); *B65D 85/50* (2013.01)

(58) Field of Classification Search
CPC ........ A01N 3/02; A01N 33/04; A01N 35/08; A01N 27/00; A01G 1/001; A01G 5/00; A01G 5/06
USPC ........... 47/58.1 CF, 58.1 R, 65.7, 65.8, 66.6, 47/66.7, 73, 79, 80, 84, 41.01; 206/204, 206/423; 426/124; 502/400, 401; 504/114, 504/115
See application file for complete search history.

(56) References Cited

U.S. PATENT DOCUMENTS

| 5,102,715 | A | 4/1992 | Zetterquist |
| 5,518,988 | A | 5/1996 | Sisler et al. |
| 5,597,632 | A | 1/1997 | Liu et al. |
| 6,017,849 | A | 1/2000 | Daly et al. |
| 6,106,775 | A | 8/2000 | Fuller |
| 6,194,350 | B1 | 2/2001 | Sisler |
| 6,340,654 | B1 | 1/2002 | Iijima |
| 6,365,549 | B2 | 4/2002 | Sisler |
| 6,797,235 | B2 | 9/2004 | Boldt |
| 7,041,625 | B2 | 5/2006 | Jacobson et al. |
| 2001/0031298 | A1 | 10/2001 | Fuller |
| 2005/0260907 | A1* | 11/2005 | Chang ............. A01N 25/34 442/62 |
| 2006/0154822 | A1 | 7/2006 | Toivonen et al. |
| 2010/0047405 | A1 | 2/2010 | Versteylen et al. |

FOREIGN PATENT DOCUMENTS

| EP | 0762829 B1 | 9/2004 |
| WO | 2008089140 A1 | 7/2008 |

OTHER PUBLICATIONS

International Search Report and Written Opinion dated Aug. 23, 2011 for corresponding International Patent Application No. PCT/US2011/036446.
International Preliminary Report on Patentability dated Sep. 7, 2012 for corresponding International Patent Application No. PCT/US2011/036446.
Stabyl et al.; "Efficacies of Commercial Antiethylene Products for Fresh Cut Flowers"; Hort Technology; Apr./Jun. 1998; pp. 1-4.
Prange et al.; "1- Methylcyclopropene: The "magic bullet" for Horticultural Products"; Chronica Horticulturae; vol. 43, No. 1, 2003; pp. 1-5.
Ethylbloc Technology; Oct. 15, 2008; www.floralife.com; p. 1.

* cited by examiner

*Primary Examiner* — Trinh Nguyen
(74) *Attorney, Agent, or Firm* — Ohlandt, Greeley, Ruggiero & Perle, LLP

(57) ABSTRACT

The present disclosure relates to prolonging shelf life of cut flowers, especially during transport, as well as enhancing physical appearance and sensory characteristics of cut flowers, by treatment systems and devices that modify the atmosphere over a longer period of time in containers in which the cut flowers are transported or stored.

17 Claims, No Drawings

TREATMENT SYSTEM TO PROLONG LIFE OF CUT FLOWERS

BACKGROUND OF THE DISCLOSURE

1. Field of Disclosure

The present disclosure generally relates to a treatment system and/or device that modifies the atmosphere in a container to prolong life of cut flowers therein.

2. Background of the Disclosure

Cut flowers are transported from flower growers around the world, frequently in South America, Europe, and Africa, to distribution centers in the U.S., Europe and Asia, then the cut flowers are further transported to florists or retail locations where they are sold to consumers. More than 65% of the cut flowers consumed in the United States at present are grown in the Andean countries. Colombia is the largest producer, followed by Ecuador, which produces primarily roses, and then Peru. African countries, such as Kenya, are another major producer of cut flowers, with the primary commercial outlet to Europe through the Netherlands. Two of the primary transit and distribution centers for cut flowers are Miami, Florida (United States) and Amsterdam (Netherlands).

The lifespan and appearance of cut flowers are negatively affected by the effects of ethylene, $C_2H_4$, a naturally-occurring hydrocarbon gas that is produced by flowers as they age and by fruit as it ripens. Ethylene is also present in the atmosphere as a reaction by-product of combustion, such as automobile exhaust, propane heater exhaust, wood smoke, and even cigarette smoke. Exposure to external ethylene in the environment can initiate internal ethylene production in some floral species. Ethylene has a "senescence effect" (also called an "aging effect") on many species of cut flowers, as well as on other plants and fruits. In some instances, the effects of ethylene can be employed to advantage, such as its use as a ripening agent for tomatoes, bananas, pears, and other fruits or vegetables after harvest. However, the effects of ethylene on cut flowers are almost all deleterious—often severely so—to the lifespan of the cut flower and its appearance. Ethylene, by binding to ethylene receptors in the cut flower, causes early senescence (i.e., a shorter flower lifespan), rapid loss of petals and leaves, (early) induction of flowering, loss of chlorophyll, epinasty (downward-bending) of leaves and stems, and dormancy, any of which can result in a loss of value of the cut flower. Furthermore, ethylene receptors are continually generated throughout the life of the flower.

As noted above, certain species of cut flowers respond to ethylene produced by external sources as well as to ethylene generated internally by the flowers themselves. Some common external sources of ethylene include ripening fruits or other plants, auto exhaust, heater exhaust, cigarette smoke, and composting vegetation. The presence of ethylene is not always easy to detect, as ethylene gas is colorless and has little or no smell, apart from a faint sweet smell that can be difficult to detect. Compounding the problem is that ethylene gas is a common air contaminant in some retail environments where cut flowers are marketed and/or displayed, such as in supermarkets, where the cut flowers may be displayed near fruits that emit large amounts of ethylene. The effects of ethylene on cut flowers may also be exacerbated when the flowers are transported in the same vehicle with other plants or fruits (such as apples) that emit large amounts of ethylene into the environment inside of the vehicle, thereby greatly reducing the shelf life and appearance of the cut flowers.

The cut flower market is intensely focused on the quality of the flower. A poor-quality flower generally cannot be sold, no matter how inexpensively the flower is priced.

The general process for transporting cut flowers is as follows: Flowers are harvested from the ground by cutting. The cut flowers are taken to a collecting center and processed for transport. The cut flowers are treated by dipping their stems dipped in a solution that kills insects and other pests, which is required for importing cut flowers into the United States and Europe. The cut flowers are cleaned, dried, and bundled. The bundles of cut flowers are placed in a shipping container for transport.

The shipping containers of cut flowers are then chilled in a refrigerator to a temperature of approximately 34° F.-40° F. (1.1° C.-4.4° C.), which decreases the rate of respiration of the cut flowers. The refrigerated shipping containers of cut flowers are then loaded on refrigerated trucks, and transported to an airport. It is believed that by the present invention the flowers could then be shipped to a seaport instead of an airport. The refrigerated shipping containers are loaded into the cargo hold of an airplane or ship, and transported to a floral transit center, such as Miami (Florida), United States, or Amsterdam, Netherlands. Upon arrival in the floral transit center, the refrigerated shipping containers of cut flowers are moved from the cargo holds of the airplane or ship to a refrigerated warehouse. The refrigerated shipping containers of cut flowers are loaded onto refrigerated trucks or other delivery vehicles for transporting to florists, retail store (e.g., supermarket or convenience store), or to local warehouses for shipping to another retail location. Upon reaching the final retail destination, the cut flowers are removed from the refrigerated shipping container, and placed in refrigerated display cases or on a retail floor for sale to consumers, who take the cut flowers home to display in a vase at room temperature. The cut flowers deteriorate rapidly after removal from a chilled environment.

Ideally, the shipping container that was packaged by the flower grower is the same container that arrives at the florist or retail outlet, without being opened to expose the contents of the shipping container and the atmosphere therein to ambient external conditions. However, in practice, shipping containers of cut flowers are opened at one or more of the transit steps. In addition, the cold chain can be violated and have the cut flowers exposed to warmer temperatures even as high as 100° F. outside of the container.

The cut flowers typically remain in the shipping container between about 5 to 7 days if shipped to a flower transit center in the U.S., but often longer if shipped to a transit center in Europe, adding even more time in the shipping container before the cut flowers arrive at their destinations where they are distributed for sale to consumers. If the cut flowers are left at the floral transit center for even an extra day or two before final trans-shipping, there are considerable losses of flowers that must be thrown away as unsellable.

SUMMARY OF THE DISCLOSURE

The present disclosure provides a treatment system and/or device that is placed in a container or box with cut flowers, especially during transport, to prolong life and physical/sensory characteristics of the cut flowers by modifying the atmosphere in the container or box.

The treatment system of the present disclosure further results in an eventual prolonged life and sensory characteristics during hydration, namely at the florist, and when in a vase at a consumer's home.

The present disclosure also provides a device for use, primarily in delivery or transportation of the flowers that holds a treatment system and provides a structure for extended release of the active agent.

The present disclosure provides such an absorbent pad device in which the rate of release and order of release of the active agents are regulated, in part, by the architectural structure of the absorbent pad, the structure and type of absorbent material used, as well as the stoichiometry and choice of reactants. A semi-permeable membrane in the absorbent pad may be used to regulate the release of active agents.

The present disclosure further provides methods of using a treatment system and device to prolong the life, physical appearance and sensory characteristics of cut flowers.

DETAILED DESCRIPTION OF THE DISCLOSURE

The treatment system and/or device of the present disclosure are placed in a shipping container (or box) with cut flowers during transport, including transportation from the grower to a retail center. This device prolongs the life of the cut flowers, and also improves their physical appearance and sensory characteristics as compared with cut flowers transported by conventional methods. This is achieved by the device's modification of the atmosphere in the shipping container or box. As used herein, prolonged life means the total life of the flower.

The treatment systems of the present disclosure allow the flower grower and processor (at the start of the supply chain) to continue to exert control over the lifespan and appearance of the cut flowers long after the shipping containers have commenced transporting. This represents a significant benefit to the flower grower and processor, who at present have little or no control over the life and appearance of the cut flowers once the shipping containers commence transportation, such as leaving the grower's dock.

The present treatment system maintains and enhances the physical appearance and sensory characteristics of a cut flower, which would include, but is not limited to: visual appearance, color, robustness, smell, freshness, and "vase life" of the cut flower. The present treatment system also slows deterioration of flowers during transport. The effects of the present treatment system on the cut flower may extend flower life, even after removal from the shipping container.

One device to achieve this increase in lifespan of cut flowers, and to maintain or enhance the sensory and physical characteristics of the cut flower, is to reduce or eliminate the effects of ethylene upon the cut flowers. The treatment systems of the present disclosure have active agents that reduce or eliminate the effects of ethylene on the cut flowers by active and/or passive mechanisms.

As used herein, a shipping container or box can be any enclosed, controlled environment that prevents passage of normal atmospheric air to cut flowers therein, but selectively provides access to the cut flowers so that flowers can be placed in, or taken therefrom. Examples of a shipping container include, but are not limited to, a cardboard box, a metal or plastic container having a cover, a sealable bag, and a closeable cooler. It should be understood that shipping container includes a container for the flowers that is simply a container that briefly stores the flowers (but is not in transport).

A typical shipping container for flowers is a cardboard box, having dimensions that are about 4 feet (4') (121.9 cm) to about five feet (5') (152.4 cm) in length by about one foot (1') (30.5 cm) in width by about 4 inches (4") (10.2 cm) to ten inches (10") (25.4 cm) in height. A preferred size of a shipping container is a cardboard box that is 41" (104.1 cm) in length×10" (25.4 cm) in width×8" (20.3 cm). Approximately 100 to 200 cut roses are typically placed in a shipping box of these dimensions.

In many embodiments of the present disclosure, the shipping container is not airtight (i.e., remains permeable to ambient air), even after the shipping container is closed and sealed around the cut flowers. However, in other embodiments of the present disclosure, the shipping container is airtight when closed and sealed to maintain the specialized atmosphere formed within the shipping container for a longer time. The treatment system and/or device of the present disclosure are able to prolong life of cut flowers, and preserve their physical appearance and sensory characteristics for a longer time, whether or not the shipping container in which the cut flowers are transported is airtight.

The present treatment system for preserving cut flowers can have one or more active agent that competitively binds to ethylene receptors to inhibit the effect of ethylene, or that chemically reacts with ethylene to reduce the levels of ethylene—or even eliminate ethylene gas altogether—from the atmosphere within the shipping container.

As noted above, the lifespan and appearance of cut flowers are unfavorably affected by the effects of ethylene, $C_2H_4$. Ethylene has a "senescence effect" (also called an "aging effect") on cut flowers. Ethylene, by binding to ethylene receptors in the flower, can cause early senescence (i.e., a shorter flower lifespan), rapid loss of petals and leaves, (early) induction of flowering, loss of chlorophyll, epinasty (downward-bending) of leaves and stems, and dormancy, any of which can result in diminution of quality, and thus a loss of value, of the cut flower.

The present treatment system can have an active agent that is one or more $CO_2$ generating system. $CO_2$ inhibits the effects of ethylene on cut flowers by changing the chemistry on the ethylene receptor site, and also dissolves into the moist part of cut flowers where it provides a bacteriostatic effect as well as interfering with ethylene binding. However, the $CO_2$ molecule diffuses from the ethylene receptor over a period of several hours, and so the effects of $CO_2$ on inhibiting ethylene are reversible over time. For this reason, the present treatment system exposes the cut flowers in the shipping container to $CO_2$ over a period of time that is sufficient to enhance preservation of cut flowers during transport.

An example of a $CO_2$ generation system for the present treatment system includes, but is not limited to, a mixture of an acid and a base. The components of the $CO_2$ generation system may be kept separate prior to activation by physical separation of the acid and base in separate pockets of the pad architecture, as described below. An alternative embodiment of a $CO_2$ generation system uses dry ice to generate $CO_2$ gas when the dry ice is exposed to temperatures that cause the ice to melt since water activates the system. In another embodiment, the $CO_2$ generation system, and/or its components, are in a laminate layer.

The acid component of a $CO_2$ generation system of the present disclosure can be an inorganic acid, an organic acid, or a combination of both. An example of an inorganic acid is boric acid. Examples of preferred organic acids include, but are not limited to, citric acid, sorbic acid, acetylsalicylic acid, fumaric acid, ascorbic acid, estearic acid, lactic acid, or any combinations thereof.

Boric acid (and its salts, such as sodium borate) is a preferred component of the present treatment system because of its bacteriostatic and antimicrobial activity, its buffering capacity, and its long use as an antimicrobial preservative in cosmetic products and pharmaceuticals. Also, boric acid does not readily penetrate intact skin, and so is relatively safe to handle with normal precautions, such as gloves, protective clothing, and eye protection.

An example of a base that can be used as part of a $CO_2$ generation system includes, but is not limited to, carbonate such as sodium bicarbonate, calcium carbonate, magnesium carbonate, or any combinations thereof.

In an exemplary embodiment of a $CO_2$ generation system, a mixture of citric acid and sodium bicarbonate can be employed. The ratio of citric acid to sodium bicarbonate is one factor (with the primary factors being the architecture of the absorbent pad and the placement and type of the active agent in the absorbent pad) that affects the amount of $CO_2$ released within the shipping container. A ratio of about 4:6 (citric acid:sodium bicarbonate) can be employed to release sufficient $CO_2$ to prolong lifespan and appearance of cut flowers. However, other ratios may be selected based on other factors, such as the $pK_a$ of the acid selected. Citric acid used in the $CO_2$ generation system provides an additional benefit, by interacting with the sodium ion of sodium bicarbonate to create a citric acid/sodium citrate buffer system to maintain the pH within the absorbent pad at levels that will not discolor or otherwise affect the appearance of the cut flowers.

Another exemplary embodiment of a treatment system of the present disclosure is one or more ethylene competitor agents. The one or more ethylene competitor agents are competitive inhibitors of ethylene; i.e., compete with ethylene to bind to ethylene receptors on the cut flower. In this way, the ethylene competitor agent operates as an "ethylene mask" that shields (or masks) a cut flower from the effects of ethylene that is produced in the vicinity of the cut flowers. The one or more ethylene competitor agents can be, but are not limited to, 1-methylcyclopropene, (also called "MCP" or "1-MCP"), or salts and/or chemical derivatives of 1-MCP. The one or more ethylene competitor agents can be selected to bind either reversibly or irreversibly to the ethylene receptors in the cut flower. The ethylene competitor agents also can be selected for persistence of binding to ethylene receptors for a period of time sufficient to extend shelf life of the flower during transport.

In a further embodiment, the present treatment system can have an agent that chemically reacts with ethylene to prevent ethylene from binding to ethylene receptors on cut flowers. An example of such an agent is a strong oxidizing agent, such as potassium permanganate ($KMnO_4$), which chemically reacts with ethylene to reduce the amount of free ethylene available to bind to ethylene receptors in the cut flowers. When used in an absorbent pad, the oxidizing agent would be placed at or near the top of the absorbent pad, where it would have the most contact with ethylene.

In another exemplary embodiment, the present treatment system can have an antimicrobial system that inhibits growth of bacteria, fungi, and viruses that can accelerate deterioration of cut flowers. The antimicrobial system can be an atmosphere modification system, including, but not limited to, $CO_2$-generating systems, $O_2$-scavenging systems, ethylene scavenging system, or any combinations thereof.

Another antimicrobial system that can be used to prolong the life of cut flowers is chlorine dioxide ($ClO_2$), which can be generated in the shipping container by one or more $ClO_2$-generating components. In an exemplary embodiment of the present treatment system, there is coated paper having a chlorine dioxide ($ClO_2$)-generating system coated thereon.

Alternatively, the $ClO_2$-generating components can be present inside the absorbent pad. Chlorine dioxide is an antimicrobial that reduces the effects of fungi (such as fungi that cause botrytis and its associated damage in cut flowers), and demonstrably changes the atmosphere in the shipping container. However, the $ClO_2$-generating system needs to be kept physically separated from water until activation since water activates the system. Also, concentrations of the components of the $ClO_2$-generating system have to be carefully regulated to prevent discoloration of the cut flowers. Thus, in this exemplary embodiment of the present treatment system that has coated paper having a chlorine dioxide ($ClO_2$)-generating system coated thereon, or its alternative (that the components that react to generate $ClO_2$ can be present in the absorbent pad), it is important that the concentrations of the components of the $ClO_2$-generating system are carefully regulated to prevent discoloration of the cut flowers.

A preferred exemplary embodiment of the present treatment system has a $CO_2$ generation system and a botrytis inhibiting agent. Examples of a botrytis inhibiting agent include, but are not limited to, sulfur dioxide ($SO_2$), chlorine dioxide ($ClO_2$)(discussed above), or any combinations thereof. Other antimicrobial gases generated in-situ may also be used, but the amount and release must be regulated to prevent discoloration of the flowers, as noted above for $ClO_2$.

Another exemplary embodiment of a treatment system of the present disclosure includes a combination of a $CO_2$ generation system and an ethylene competitor agent, to increase the lifespan of cut flowers, and/or enhance their physical appearance and sensory characteristics. An embodiment of the present treatment system is a combination of MCP and a $CO_2$ generation system that is citric acid and sodium bicarbonate. Another embodiment is a combination of MCP and a $CO_2$ generation system that is boric acid and sodium bicarbonate.

The presence of $CO_2$ in the atmosphere in the shipping container does not interfere with the efficacy of MCP, so that both gases inhibit the ethylene response in cut flowers.

An exemplary embodiment of the present treatment system has a combination of a $CO_2$ generation system and a compound that is an ethylene competitor, such as MCP. This combination has been observed to result in an increase in the lifespan of cut roses of approximately two days. This is surprising since it is believed that by interfering with the ethylene receptors, $CO_2$ would also prevent the ethylene competitor, MCP, from binding. However, since the ethylene competitor is developed in a burst over a short period of time and then dissipates, while $CO_2$ is generated over a longer period of time and its effects become significant after the ethylene competitor has finished or dissipated.

In another embodiment, the MCP precursors are distributed throughout the pad architecture in such a manner that the gas is generated in stages as the activation liquid travels though the layers of the pad. An absorbent pad containing creped tissue fosters migration of liquids and/or moisture in both the horizontal and vertical axes of the absorbent pad. As the liquid and/or moisture is distributed horizontally, the active chemicals or precursors on any given layer of the pad are activated. Vertical migration of liquids and/or moisture will carry one active component to another active component positioned on a different level of the pad architecture. In this way, the rate and duration of gas generation can be controlled and prolonged by the use of membranes that control vertical migration, the stoichiometry and amount of the active agents, and placement of active components in the different layers of the absorbent pad.

Still another exemplary embodiment of the present treatment system has a $CO_2$ generation system, without another active agent.

Yet another embodiment of the present treatment system has an $SO_2$ generation system, either alone or with another active agent. An exemplary embodiment of an $SO_2$ generation system includes, but is not limited to, sodium metabisulfite ($Na_2S_2O_5$), which reacts with water and/or moisture to generate $SO_2$. Another exemplary embodiment of the present treatment system has a $CO_2$ generation system and an $SO_2$ generation system; and another exemplary embodiment of the present treatment system has a $CO_2$ generation system, an $SO_2$ generation system, and an ethylene competitor, such as MCP.

A further exemplary embodiment of the present treatment system has an $SO_2$ generation system and an ethylene competitor, such as MCP.

Yet a further exemplary embodiment, the present treatment system has a $CO_2$ generation system and a superabsorbent material, where the superabsorbent material operates as a reservoir for water that activates the $CO_2$ generation system and also as a source of water vapor (moisture) in the shipping container to hydrate the cut flowers so the flowers do not dry out during transport. Examples of superabsorbent material include, but are not limited to, superabsorbent polymer such as polyacrylate (and its laminates with cellulose, airlaids or non-wovens). A preferred exemplary embodiment has a $CO_2$ generation system and a starch-based superabsorbent material, such as BioSAP™ (Archer-Daniels Midland, Decatur, Ill.), which is a renewable resource.

In yet another exemplary embodiment of the present treatment system, there is a compound that is an ethylene competitor that is contained in an absorbent pad, as described below. As an example, the ethylene competitor can be, but is not limited to, MCP.

In still another exemplary embodiment of the present treatment system, there is a $CO_2$ generation system in combination with $KMnO_4$ in an absorbent pad described below, where the components of the $CO_2$ generation system and $KMnO_4$ are held in separate pockets of the absorbent pad prior to activation.

The treatment systems of the present disclosure, used alone or in combination, have the advantage of operating well in chilled (refrigerated) temperatures. As noted above, cut flowers are shipped in chilled temperatures between 34° F.-40° F. (1.1° C.-4.4° C.) to decrease respiration of the flowers, and preserve their lifespan, physical appearance, and sensory attractiveness (e.g., floral "smell"). The treatment systems of the present disclosure are operable below 32° F. (0° C.), although cut flowers are generally not transported below the freezing temperature of water because of unfavorable effects on flower appearance.

The present disclosure includes a device that holds the one or more active agents in the treatment system, and/or holds a reservoir of water that activates the treatment system and is a source of humidity (i.e., water vapor), to prolong the life of cut flowers and enhance their physical appearance and sensory properties. Examples of such a device include, but are not limited to, an absorbent pad, sachet, composite material, coated paper (having active agents in the coating), or any combinations. Preferably, the device is an absorbent pad.

An absorbent pad can have an architecture that is structured to control the release profile of the one or more active agents held therein, including providing for extended release of the active agent in the atmosphere of the shipping container for cut flowers.

The specific architecture and structure of the absorbent pad, including the type and quantity of the absorbent layer(s), top and bottom layers, and placement of one or more active agents in the absorbent pad in relation to the absorbent layers, controls the activity and availability of the one or more active agents to preserve and enhance freshness of cut flowers in a shipping container. The top layer can be a film, such as polyethylene, polypropylene, polyester, or a non-woven material, CFT, or any material permeable to a liquid or a gas, and is preferably a polyethylene film. The bottom layer can be a non-woven material or film, and is preferably a non-woven material. As used in this disclosure, the "architecture" of an absorbent pad means the structure and order of individual layers of absorbent material and one or more active agents therein.

An absorbent pad of the present disclosure can have an absorbent body made of one or more absorbent layers. In an exemplary embodiment, the one or more absorbent layers are one or more tissue layers. A preferred embodiment has one or more cellulose tissue layers.

Tissue layers provide the advantage of uniform distribution of all absorbed liquids throughout the pad, end-to-end. For example, a cellulose tissue layer is made of cross-linked fibers, whereby any absorbed liquid is distributed, fiber-to-fiber, horizontally across the plane of the tissue layer from one end of the absorbent body to its opposite end, as well as widthwise from one edge to its opposite edge. In addition, in those embodiments where a second tissue layer or even a third tissue layer are adjacent the first tissue layer in the pad architecture, any absorbed liquid will also distribute vertically, from fiber-to-fiber, from the tissue fibers in the first tissue layer to tissue fibers present in the adjacent tissue layers. This distribution of absorbed liquid thus can go on horizontally from end-to end and edge-to-edge in each tissue layer, as well as vertically between adjacent tissue layers, so that, if sufficient liquid is absorbed, the entire absorbent pad can be uniformly "wetted" with absorbed water or other liquid that is then available to activate one or more active agent also present in the pad architecture. That is, absorbed water or other liquid is distributed three-dimensionally by employing layers of absorbent tissue placed adjacent each other.

Tissue layers distribute absorbed water or other liquids horizontally (i.e., across the plane of the tissue layer), as well as distribute those absorbed liquids vertically (i.e., from one tissue layer to an adjacent tissue layer). This is an advantage over fluff absorbent material, which can form into "clumps" of fluff having spaces therebetween, which cannot distribute moisture uniformly across the pad due to the spaces in the pad architecture where there is little or no fluff. An exemplary embodiment of an absorbent pad having tissue layers is 15% lighter, yet 17% more absorbent, than a comparable-sized pad using fluff material for absorbency. Similarly, some superabsorbent polymers (SAP), when used as an absorbent material, retain the water or other absorbed liquid in the SAP molecule, and prevent the water from being distributed across the pad horizontally or vertically.

As used herein, "activation speed" is the rate at which an active agent (or combination of reagents that, when contacted with each other, combine to form an active agent) is activated by contact with a liquid, such as water, to exert an effect on prolonging the life and/or appearance of cut flowers. Activation speed can be increased or reduced by careful selection of the number of tissue layers in the pad architecture, the thickness or density of each tissue layer, and/or the material(s) used to make the tissue layer. Activation speed can be further regulated by adding one or more semi-permeable membrane in the architecture of the absorbent pad.

The rate of release and order of release of the active agents are regulated, in part, by the architectural structure of the absorbent pad, the structure and type of absorbent material used, the stoichiometry and choice of reactants, and the selective permeability of a membrane in the absorbent layer.

The one or more absorbent layers may be arranged to form separate pockets or compartments in the absorbent pad. As used herein, a "pocket" means an area between two layers that can hold in place one or more active agents. A pocket can be an area between two adjacent tissue layers, between a top layer and adjacent tissue layer, and/or between a bottom layer and adjacent tissue layer. One or more pockets can be arranged in the architecture of the absorbent pad to hold one or more active agents before release, thereby controlling the availability and timing of release of the one or more active agent therein.

Another pad architecture that can regulate the release of active agents is a semi-permeable membrane. An example of a semi-permeable membrane is a nonwoven. The nonwoven can have a pore size that can regulate the passage speed of absorbed water or other liquid through the pad architecture, typically vertically. The pore size can be sized by selecting the density and weight of the nonwoven, or other material for the semi-permeable membrane, since the interaction of fibers of nonwoven will form the pore. Nonwoven fibers are projected from a nozzle in random fashion to form a nonwoven. Where three or more fibers interact, such as a triangular form, a hole ("pore") is formed. Using a greater density or weight of fibers generally leads to formation of a nonwoven having a smaller pore size. In an exemplary embodiment, using a nonwoven material of high density or high weight will form a nonwoven with a small pore size. Generally, there is a direct correlation between a pore size and the passage rate of the water or other absorbed liquid. For example, a nonwoven having a small pore size will cause a slower passage rate of water or other absorbed liquids therethrough. However, in addition to pore size, passage speed may be otherwise increased or slowed by addition of a surfactant.

In another exemplary embodiment, the semi-permeable membrane itself may contain an active agent. The pad architecture may contain one or more semi-permeable membranes therein to regulate the activation rate and controlled release, such as delayed release, extended release, or sustained release. For example, pad architecture may be selected to cause a "staged" release of active, whereby separate portions of the active are released in different time periods).

The layers in the absorbent pad hold the one or more active agents in the treatment system, and keep the one or more active agents separated. The absorbent layers also hold water that activates the one or more active agents in the absorbent pad, and also operates as a reservoir of humidity (water vapor) to help maintain hydration (i.e., reduce drying out) of the cut flowers during transport.

The absorbent body may be a material such as fluff pulp, cellulose, airlaid, nonwoven, paper, binding fiber, woven, polymer, absorbent gels, superabsorbent polymer (SAP), compressed SAP, composite of SAP granules adhered with one or more binders or plasticizers, airlaid with SAP, compressed composite with short or microfiber materials, thermoplastic polymer fibers, cellulose powders, or any combinations. An example of non-woven material is spun-bonded polypropylene or perforated plastic film. Examples of superabsorbent material include, but are not limited to, superabsorbent polymers such as polyacrylate (and its laminates with cellulose, airlaids or non-wovens), or starch-based superabsorbent materials that are biodegradable and compostable, such as BioSAP™ (Archer-Daniels Midland, Decatur, Ill.).

The absorbent pad can be structured so that the one or more active agent is not expended during initial activation but is available to regenerate an atmosphere in the shipping container that prolongs the life and appearance of cut flowers after the shipping container has been opened and re-closed.

The absorbent pad of the present disclosure may be secured to the shipping container by one or more securing device, or may be unattached to the shipping container and simply placed therein, among the cut flowers. The one or more securing device, where present, can be on the absorbent pad, on the shipping container, or a combination of both.

As will be illustrated by several exemplary embodiments in this application, the one or more active agents, or even the individual components that make up a single type of active system (such as the individual chemical components of a $CO_2$ generation system) can be separated by absorbent tissue layers in the structure of the absorbent pad, laminate, or other material with limited or specific permeability, such that there is an immediate release or "burst" of $CO_2$ in the shipping container, and also an extended release or "delayed burst" of $CO_2$ at a later time, i.e., when a different pocket of $CO_2$-generating components is activated by contact with water. The separate bursts of $CO_2$ in the shipping container help to preserve and extend the lifespan of cut flowers and thereby reduce wastage.

The present disclosure contemplates a treatment system that is capable of regenerating an atmosphere in the shipping container after the shipping container has been opened and re-closed to add or remove cut flowers (i.e., re-introducing the ambient environment into the interior of the shipping container). An absorbent pad having one or more active agents positioned in separate pockets or in different layers of the pad architecture, possesses the capability for unexpended active agents to be activated after the shipping container is re-closed, and to regenerate an atmosphere in the shipping container that will be favorable to the lifespan and appearance of cut flowers therein.

In an exemplary embodiment, the device can be "wetted" by spraying water thereon before the shipping container is closed. Additional water is absorbed or adsorbed by the device from water dripping from the cut flowers. The water in the device operates as a reservoir of water that activates the one or more treatment systems and as a source of moisture (water vapor) inside the shipping container to keep the flowers hydrated. In an exemplary embodiment, the device is an absorbent pad that is sprayed with about 20 mL of water before the shipping container is closed. However, the amounts of water sprayed onto the device for this "pre-wetting" depends on the species of cut flower, the number and size of devices, and the expected duration of transport.

The present treatment system offers the benefit of reducing the amounts of the greenhouse gas $CO_2$ as compared with conventional approaches where entire warehouses storing cut flowers are filled with an increased amount of $CO_2$. Using the treatment systems of the present disclosure, the shipping containers for the cut flowers can be filled with $CO_2$ rather than the entire warehouse, greatly reducing the overall amounts of $CO_2$ used to prolong life of a given number of cut flowers. In addition, delivering $CO_2$ by extended release from a device placed within a shipping container conserves the generated $CO_2$ (reducing losses from escape of gas as compared with pumping large volumes of $CO_2$ through a warehouse) which is available to compete with ethylene for a longer time. Since $CO_2$ is marginally heavier than air, the present device placed in the bottom of a shipping container, when activated by wetting the pad, fills the shipping container with $CO_2$. Thus, the treatment systems and methods of the present disclosure can significantly reduce the amounts of $CO_2$ released into the atmosphere as compared with amounts released by conventional transport of cut flowers.

Pad architecture, stoichiometry of the reactants (and selection of which reagent is in excess), permeability of the membrane, and choice of reactants) can be customized to provide the amount and duration of release of $CO_2$ (and/or $SO_2$, and/or $ClO_2$, and/or an ethylene competitor), based on the species of cut flower, which may have different sensitivities to ethylene.

The present disclosure further provides a method of using a treatment system and/or device in a shipping container or box for cut flowers, that, as stated above, prolongs the life of cut flowers during transport, as well as preserve the physical appearance and sensory characteristics of the cut flowers for a longer time as compared with conventional transport. The method includes the steps of placing one or more treatment system/device in a shipping container of cut flowers before closing the shipping container. The treatment system/device can be activated by wetting the device by spraying water or solution thereon, or dipping the device into it. Alternatively, water that drips from the cut flowers in the shipping container can be absorbed by the device to serve as a water reservoir to activate the one or more treatment systems and to humidify the interior of the shipping container to reducing drying of the cut flowers during transport.

EXPERIMENTAL

The following study was conducted to evaluate the effect of five (5) different treatments delivered in the form of pads that were placed inside of containers or boxes for shipping flowers from a flower grower in South America to the United States versus flowers in a box that were shipped with no control, namely no pad. The pads containing the treatment systems were made in California, and labeled "A" through "E." The study participants were only aware that the pads were labeled "A" through "E," but not the active agent(s) corresponding to each treatment.

There were eleven (11) boxes of cut flowers packaged for each of the five treatments and another eleven boxes of cut flowers as controls, thus a total of sixty-six boxes (66). One (1) pad was placed in each treatment box of flowers at the processing facility prior to shipment. Temperature and Relative Humidity (RH) recorders were randomly placed in certain boxes at that same time. Those recorders stayed with the flowers until the flowers were taken out of the box.

A first set of the boxed flowers once received in the U.S. were sent to five different locations for evaluation:
(A) One (1) box of each treatment and a control in Miami (total of 6);
(B) One (1) box of each treatment and a control in Chicago, Ill. (total of 6);
(C) One (1) box of each treatment and a control was sent to a private retail florist, Dixon, Ill. (total of 6);
(D) One (1) box of each treatment and a control was sent to Paper-Pak Industries Laboratory, LaVerne, Calif. (total of 6);
(E) Three (3) boxes of each treatment and three controls were sent for evaluation to a laboratory at the California Polytechnic State University (Cal Poly Lab), St. Luis Obispo, Calif. (total of 18).

A second set, subsequently received, in the U.S. were shipped as follows:
(A) One (1) box of each treatment and control remained in Miami (total of 6);
(B) One (1) box of each treatment and control was sent to Chicago, Ill. (total of 6);
(C) One (1) box of each treatment and control was sent to a private retail florist, Dixon, Ill. (total of 6);
(D) One (1) box of each treatment and control was sent to Paper-Pak Industries Laboratory, LaVerne, Calif. (total of 6);

Evaluation

Flowers were evaluated by a sensory evaluation on a hedonic scale of 1 through 9, where 1 is a flower in the worst condition, 9 represents perfect condition, and 5 is borderline.

Both sets of flowers were evaluated at the Warehouses in Chicago and Miami, as follows: Flowers were handled according to normal procedures and kept until considered non-sellable. The time at which the flower became non-sellable was recorded for each one of the treatments and control. The state of the flowers was documented by taking a photograph and writing a short description of the status based on hydration, color, transparency, hardness, etc.

The flowers evaluated at the Paper-Pak Industries Laboratory were as follows for both the first and second sets. 15 flowers each went into 4 vases with 2 of those 4 vases immediately placed into refrigeration and the other 2 vases immediately placed into room temperature. At day 7, the 2 refrigerated vases, were placed in room temperature. Temperature and relative humidity (RH) were monitored daily for the first set. The changes were recorded by taking photographs every other day. Also, the opening of the buds was measured on the same day that photos were taken.

Flowers were evaluated at the Cal Poly Lab using the same initial and at day 7 protocol used at Paper-Pak Industries Laboratory. The goal was to develop a quantifiable model to evaluate the flower development. Several parameters were measured: color; opening of the buds; yellowing of the leaves' time at which petals fall. For comparison purposes, photographs were also taken every other day. Cal Poly Lab performed an evaluation to determine if the variations observed were statistically significant.

Flowers were also evaluated at the retail florist in Dixon, Ill., for a point-of-sale evaluation, as follows. Upon receiving the flowers from the first set, the flowers from each box were separated into three equal groups. The first group was placed in vases at room temperature, the second group was placed in a treated cooler, and the third group was placed in an untreated cooler. Each group included the five treatments plus control and was maintained in one vase, and all treatments and control were placed under the same conditions. By day 7, the other two groups were brought from the cooler and placed into vases at room temperature. Temperature and relative humidity (RH) were monitored during this time. The changes were recorded by taking daily photographs of the five groups. Upon receiving the flowers from the second set, the above steps were repeated.

The results of this study showed that, of the five treatments studied, cut flowers that were transported in a container with an absorbent pad having a $CO_2$ generation system (only) or an absorbent pad having a $CO_2$ generation system and an ethylene competitor had the longest shelf-life and overall acceptability as compared with the control group.

The word "about," as used herein for dimensions, weights, or measures of absorbency, means a range that is ±10% of the stated value, more preferably ±5% of the stated value, and most preferably ±1% of the stated value, including all subranges therebetween.

It should be understood that the foregoing description is only illustrative of the present disclosure. Various alternatives and modifications can be devised by those skilled in the art without departing from the disclosure. Accordingly, the present disclosure is intended to embrace all such alternatives, modifications, and variances that fall within the scope of the disclosure.

What is claimed is:

1. An absorbent pad that prolongs the life of a cut flower in a container used for transport or storage of the cut flower, said absorbent pad comprising:
    a top layer;
    a bottom layer;
    an absorbent body positioned between said top layer and said bottom layer, said absorbent body comprising a layer of an absorbent material; and
    a first active agent and a second active agent each in said absorbent body, wherein said first active agent is a compound that is an ethylene competitor, and wherein said second active agent is a carbon dioxide ($CO_2$) generation system,
    wherein said absorbent pad initiates release of said first and second active agents in the container upon contact with water, and
    wherein said first and second active agents prolong the life of the cut flower.

2. The absorbent pad according to claim 1, wherein said layer of absorbent material is two or more tissue layers positioned adjacent to each other, and wherein each of said two or more tissue layers are a continuous layer that distributes an absorbed liquid across the axial extant thereof.

3. The absorbent pad according to claim 2, wherein said two or more adjacent tissue layers distribute an absorbed liquid between each other.

4. The absorbent pad according to claim 1, wherein said first and second active agents inhibit the effects of ethylene on the cut flower.

5. The absorbent pad according to claim 1, further comprising a third active agent in said absorbent body, wherein said third active agent is selected from the group consisting of sulfur dioxide ($SO_2$) generation system, chlorine dioxide ($ClO_2$) generation system, oxygen ($O_2$) scavenging system, oxidizing agent, and any combinations thereof.

6. The absorbent pad according to claim 1, wherein said $CO_2$ generation system comprises an acid and a base, and wherein said acid is selected from the group consisting of boric acid, citric acid, lactic acid, sorbic acid, acetylsalicylic acid, fumaric acid, ascorbic acid, estearic acid, and any combinations thereof.

7. The absorbent pad according to claim 1, wherein said ethylene competitor is 1-methylcyclopropene (MCP), its salts, or derivatives.

8. The absorbent pad according to claim 1, wherein said absorbent body holds a reservoir of absorbed water that is a source of water to activate said first and second active agents and is a source of water vapor that enhances the physical appearance and sensory properties of the cut flower, and prolongs the life of the cut flower.

9. A treatment system to prolong the life of a cut flower, said treatment system comprising:
    a container used for transport or storage of said cut flower, wherein said container can be opened and re-closed to permit ingress and egress of said cut flower in said container;
    an absorbent pad placed in said container, said absorbent pad comprising:
        a top layer;
        a bottom layer;
        an absorbent body positioned between said top layer and said bottom layer, said absorbent body comprising one or more layers of an absorbent material; and
        a first active agent and a second active agent each in said absorbent body, wherein said first active agent is a compound that is an ethylene competitor, and wherein said second active agent is a carbon dioxide ($CO_2$) generation system,
    wherein said absorbent pad initiates release of said first and second active agents in said container upon contact with water to maintain the physical appearance and sensory characteristics of said cut flower.

10. The treatment system according to claim 9, wherein said absorbent pad in said container reduces the total amount of $CO_2$ required to prolong the life of said cut flower.

11. A method for prolonging the life and physical appearance of a cut flower in a container, comprising:
    placing an absorbent pad in the container, said absorbent pad comprising:
        a top layer;
        a bottom layer;
        an absorbent body positioned between said top layer and said bottom layer, said absorbent body comprising one or more layers of an absorbent material; and
        a first active agent and a second active agent each in said absorbent body, wherein said first active agent is a compound that is an ethylene competitor, and wherein said second active agent is a carbon dioxide ($CO_2$) generation system;
    placing one or more cut flowers in the container; and
    closing the container to enclose said one or more cut flowers.

12. The method according to claim 11, further comprising wetting said absorbent pad by spraying water thereon prior to closing the container.

13. The method according to claim 11, wherein said first and second active agents are a combination of compounds that inhibit the effects of ethylene on said one or more of said cut flowers.

14. The method according to claim 11, further comprising a third active agent in said absorbent body, wherein said third active agent is selected from the group consisting of sulfur dioxide ($SO_2$) generation system, chlorine dioxide ($ClO_2$) generation system, oxygen ($O_2$) scavenging system, oxidizing agent, and any combinations thereof.

15. The absorbent pad according to claim 11, wherein said $CO_2$ generation system comprises an acid and a base, and wherein said acid is selected from the group consisting of acetylsalicylic acid, fumaric acid, estearic acid, and any combinations thereof.

16. The absorbent pad according to claim 14, wherein said third active agent is an oxidizing agent placed near said top layer of said absorbent pad.

17. The absorbent pad according to claim 1, further comprising a semi-permeable membrane positioned in said absorbent body, said semi-permeable membrane having one or more pores of a size that regulates the rate at which liquid is absorbed and distributed throughout said absorbent body.

* * * * *